(12) United States Patent
Verma

(10) Patent No.: US 11,676,727 B2
(45) Date of Patent: Jun. 13, 2023

(54) COHORT-BASED PREDICTIVE DATA ANALYSIS

(71) Applicant: Optum Technology, Inc., Eden Prairie, MN (US)

(72) Inventor: Neeraj Verma, Greater Noida (IN)

(73) Assignee: Optum Technology, Inc., Eden Prairie, MN (US)

( * ) Notice: Subject to any disclaimer, the term of this patent is extended or adjusted under 35 U.S.C. 154(b) by 690 days.

(21) Appl. No.: 16/540,518

(22) Filed: Aug. 14, 2019

(65) Prior Publication Data

US 2021/0050110 A1 Feb. 18, 2021

(51) Int. Cl.
   *G16H 50/30* (2018.01)
   *G16H 10/60* (2018.01)
   *G16H 50/70* (2018.01)

(52) U.S. Cl.
   CPC .......... *G16H 50/30* (2018.01); *G16H 10/60* (2018.01); *G16H 50/70* (2018.01)

(58) Field of Classification Search
   CPC ......... G16H 50/30; G16H 10/60; G16H 50/70
   See application file for complete search history.

(56) References Cited

U.S. PATENT DOCUMENTS

| | | |
|---|---|---|
| 2002/0077756 A1 | 6/2002 | Arouh et al. |
| 2006/0173663 A1 | 8/2006 | Langheier et al. |
| 2009/0171697 A1 | 7/2009 | Glauser et al. |
| 2009/0204430 A1 | 8/2009 | Gliklich |
| 2010/0332443 A1 | 12/2010 | Gartenberg |

(Continued)

FOREIGN PATENT DOCUMENTS

| | | |
|---|---|---|
| WO | 2018/134682 A1 | 7/2018 |
| WO | 2018/160548 A1 | 9/2018 |

OTHER PUBLICATIONS

Aggarwal, Shilpi et al. "EGLN1 Involvement In High-Altitude Adaptation Revealed Through Genetic Analysis of Extreme Constitution Types Defined In Ayurveda," Proceedings of the National Academy of Sciences, vol. 107, No. 44, Nov. 2, 2010, pp. 18961-18966. [Retrieved from the Internet Nov. 14, 2019] <https://www.pnas.org/content/107/44/18961 >.

(Continued)

*Primary Examiner* — Jay M. Patel
(74) *Attorney, Agent, or Firm* — Alston & Bird LLP

(57) ABSTRACT

There is a need for more effective and efficient predictive data analysis solutions. This need can be addressed by, for example, obtaining prediction input objects each associated with a predictive entity; performing iterations of an iterative cohort generation routine until a qualified predictive model is identified, wherein each iteration comprises determining one or more predictive cohorts for predictive entities based on the prediction input objects, generating a predictive model based on the predictive cohorts, performing a predictive inference based on the predictive model to generate a current iteration prediction, generating a predictive score based on the current iteration prediction, and determining whether the predictive model is the qualified predictive model based on whether the predictive score exceeds a predictive score threshold; and performing cohort-based predictive data analysis based on the qualified predictive model to generate a respective final prediction for each predictive entity.

17 Claims, 11 Drawing Sheets

(56) References Cited

U.S. PATENT DOCUMENTS

| | | | |
|---|---|---|---|
| 2012/0046965 A1* | 2/2012 | Ryan | G16Z 99/00 705/2 |
| 2014/0046696 A1 | 2/2014 | Higgins et al. | |
| 2014/0052465 A1 | 2/2014 | Madan et al. | |
| 2014/0236630 A1* | 8/2014 | Murata | G16H 10/60 705/3 |
| 2014/0372138 A1* | 12/2014 | Chari | G16H 40/20 705/2 |
| 2015/0122694 A1 | 4/2015 | Blake et al. | |
| 2015/0193583 A1* | 7/2015 | McNair | G16H 50/20 705/2 |
| 2015/0227710 A1* | 8/2015 | Pappada | G16H 70/20 705/2 |
| 2016/0328526 A1 | 11/2016 | Park et al. | |
| 2017/0154162 A1* | 6/2017 | Balasubramanian | G16H 50/30 |
| 2018/0300456 A1 | 10/2018 | Eltoukhy et al. | |
| 2018/0330824 A1 | 11/2018 | Athey et al. | |
| 2019/0156193 A1* | 5/2019 | Jaroch | G06N 3/045 |

OTHER PUBLICATIONS

Govindaraj, Periyasamy et al., "Genome-Wide Analysis Correlates Ayurveda Prakriti," Scientific Reports 5, Article No. 15786, Oct. 29, 2015, pp. 1-12. [Retrieved from the Internet Nov. 14, 2019] <https://www.nature.com/articles/srep15786>.

Prasher, Bhavna et al. "Whole Genome Expression and Biochemical Correlates of Extreme Constitutional Types Defined in Ayurveda," Journal of Translational Medicine, vol. 6, Article No. 48, Sep. 9, 2008, pp. 1-12. [Retrieved from the Internet Nov. 14, 2019] <https://translational-medicine.biomedcentral.com/articles/10.1186/1479-5876-6-48>.

Tiwari, Pradeep et al. "Recapitulation of Ayurveda Constitution Types By Machine Learning Of Phenotypic Traits," PloS One, vol. 12, No. 10, Oct. 5, 2017, pp. 1-17. [Retrieved from the Internet Nov. 14, 2019] <https://journals.plos.org/plosone/article?id=10.1371/journal.pone.0185380>.

International Searching Authority, International Search Report and Written Opinion for International Application No. PCT/US2020/042023, dated Oct. 27, 2020, (15 pages), European Patent Office, Rijswijk, Netherlands.

\* cited by examiner

| S.No. | Question/Parameter | a | b | c |
|---|---|---|---|---|
| 1 | Contentment | Absent | Absent | Full contented/satisfied |
| 2 | Conscience | Wavering or no conscience | Follows to some extent | Follows totally |
| 3 | Forgiving nature | Absent | Absent | Present |
| 4 | Will Power | Lack | Fair | Good |
| 5 | Aggressiveness | Aggressive, Violent | Varied (aggressive for those who do not agree or surrender, however sympathizes with surrendered) | Not aggressive |
| 6 | Friendship | Very Few, very short relationships | Few friends | Many and lasting relationships |
| 7 | Theism | Non-religious | Usually non-religious | Religious |
| 8 | Memory | Poor | Fair | Good |
| 9 | Concentration | Unable to focus | Fairly well | Good |
| 10 | Grasping power | Quick | Intermediate | Takes long |
| 11 | Planning | Short Term | Short Term | Long term, far sighted |
| 12 | Helping attitude | Absent | Help upon ask | General Helping attitude |
| 13 | Conduct | Uncultured | Good Conduct | Good |
| 14 | Respect for teachers/elders | No respect | Some Respect | Respect |

FIG. 5A

| | | | |
|---|---|---|---|
| 15 | Desires and Likes | Music, Laughter, hunting, arts | Flowers, application of pastes on the body | Scientific, philosophical literature, music |
| 16 | Climate and food | Hot, humid | Cold | Warm |
| 17 | Irritability | Quickly excited | Quickly excited | Calm, not crying excessively even in infancy |
| 18 | Jealousy | Jealous | Jealous, envy in excess | Minimum |
| 19 | Anger | Quickly gets angry for short duration | Quickly gets angry and in excess | Does not get angry usually but lasts long |
| 20 | Happiness and Mood | Changing moods | Changing moods (gets happy quickly) | Steady mood, generally happy |
| 21 | Love | Fall a prey to sex instinct | Moderate control over sex urge | Good control |
| 22 | Fear | Fearful | Frightened Quickly | Minimum |
| 23 | Speech | Talkative, incoherent speech | Insulting speech | No offensive speech, consistent and thoughtful |
| 24 | Ability to tolerate exertion (mental & physical) | Low | Low | High |
| 25 | Gait (Walk) | Fast, unsteady | Moderate | Slow and steady |
| 26 | Beginning of an Activity | Quick | Moderate | Slow |
| 27 | Energy | Moderate | Moderate | Energetic |
| 28 | Build and S | Tall, thin, poorly built, Parts of the body not proportionate at times | Delicate, Medium built, flabby | Large well built, proportionate body parts |

FIG. 5A-1

| S.No. | Question/Parameter | a | b | c |
|---|---|---|---|---|
| 29 | Strength | Weak | Moderate | Strong |
| 30 | Skin | Dry, Rough, Thin, cracked, prominent veins | Soft, thin, warm wrinkled, with pink, reddish, many moles and eruptions | Soft, luster, wet, cold skin |
| 31 | General Appearance | Dry, emaciated, not pleasant | In between | Pleasant appearance |
| 32 | Voice | Rough, high pitched, unclear, fast speech | Clear, high pitched | Deep, pleasant resonating |
| 33 | Color | Dark | White | Fair |
| 34 | Forehead | Small | Medium | Large |
| 35 | Shoulder and Chest | Small | Medium | Large, fleshy |
| 36 | Eyes | Unsteady, dry, lusterless, remain partially open while sleeping, sunken | Normal, unable to bear light, small | Big eyes, dull, watery and well differentiated sclera and iris |
| 37 | Eyelashes | Thin, Scanty and dry | Thin, scanty | Long, Oily |
| 38 | Teeth | Rough, Small, gritting of teeth, appears dry | White | Shiny |

FIG. 5B

| | | | |
|---|---|---|---|
| 39 Tongue | Dry, cracked, rough | Red, dark | White, Slimy |
| 40 Mouth | Dry, Astringent taste | Red palate, Bitter or Sour | Excessive salivation, sweet taste |
| 41 Limbs | Thin, rough | Red palm and soles | Long unctuous smooth limbs |
| 42 Veins | Prominent | Intermediate | Well covered |
| 43 Abdomen Muscles | Sunken, poorly built | Moderately built | Bulging, flabby |
| 44 Joints | Not well placed, sounds on movement | Soft, loose ligaments | Joints deep and well placed |
| 45 Weights | Light | Medium | Heavy |
| 46 Hair | Dry, Rough, thin, less | Early greying of hairs, less in number, baldness, soft thin | Strong, dark, long, good growth |
| 47 Nails | Dry, Small, rough, discolored, cracked | Pinkish | Soft, white, oily |
| 48 Appetite | Irregular, eating small quantities frequently | Eating large quantity of food frequently | Less appetite |
| 49 Thirst | Thirsty | Thirsty | Less thirsty |
| 50 Sleep | Less, disturbed (6 hours) | Moderate (6-8 hours) | Sleepy, loves sleep (8 hours or |
| 51 Pulse | Fast | Fast | Slow |
| 52 Perspiration | Less | Excessive | Less |
| 53 Bowel movements | Constipation | Large quantity of stool and tendency for increased number of times | Normal |
| 54 Menstrual Flow (women only) | Scanty and dark flow | Profuse, red and foul smell | Moderate flow |
| 55 Semen (Men) | Scanty | Scanty | Profuse |

COHORT-BASED PREDICTIVE DATA ANALYSIS

BACKGROUND

Various embodiments of the present invention address technical challenges related to performing predictive data analysis in high-dimensionality and/or highly sparse input spaces. Existing predictive data analysis systems are ill-suited to efficiently and reliably perform predictive data analysis in high-dimensionality and/or highly sparse input spaces. Various embodiments of the present address the shortcomings of the noted existing predictive data analysis systems and disclose various techniques for efficiently and reliably performing predictive data analysis in high-dimensionality and/or highly sparse input spaces.

BRIEF SUMMARY

In general, embodiments of the present invention provide methods, apparatus, systems, computing devices, computing entities, and/or the like for predictive data analysis in high-dimensionality and/or highly sparse input spaces. Certain embodiments utilize systems, methods, and computer program products that cohort-based predictive data analysis as well as external integration of cohort-based predictive models.

In accordance with one aspect, a method is provided. In one embodiment, the method comprises receiving a plurality of prediction input objects, wherein each of the plurality of prediction input objects is associated with a predictive entity of a plurality of predictive entities; for each entity-factor pair associated with a predictive entity and a predictive factor, generating a factor score indicating a predicted entity-factor relevance of the predictive factor to the corresponding predictive entity based at least in part on the predictive input object associated with the corresponding predictive entity; performing at least one iteration of an iterative cohort generation routine until a qualified predictive model is identified, wherein each iteration of the at least one iteration comprises determining one or more predictive cohorts of the plurality of predictive entities for the current iteration based at least in part on each factor score associated with an entity-factor pair, wherein each predictive cohort of the one or more predictive cohorts is associated with a factor range for each predictive factor of the plurality of predictive factors, generating a predictive model for the current iteration based at least in part on the one or more predictive cohorts for the current iteration, performing a predictive inference for the current iteration based at least in part on the predictive model for the current iteration to generate a current iteration prediction for the current iteration, generating a predictive score for the current iteration based at least in part on the current iteration prediction for the current prediction, and determining whether the predictive model for the current iteration is the qualified predictive model based at least in part on the predictive score for the current iteration; and performing the cohort-based predictive data analysis based at least in part on the qualified predictive model to generate a respective final prediction for each predictive entity of the plurality of predictive entities.

In accordance with yet another aspect, an apparatus comprising at least one processor and at least one memory including computer program code is provided. In one embodiment, the at least one memory and the computer program code may be configured to, with the processor, cause the apparatus to receive a plurality of prediction input objects, wherein each of the plurality of prediction input objects is associated with a predictive entity of a plurality of predictive entities; for each entity-factor pair associated with a predictive entity and a predictive factor, generate a factor score indicating a predicted entity-factor relevance of the predictive factor to the corresponding predictive entity based at least in part on the predictive input object associated with the corresponding predictive entity; perform at least one iteration of an iterative cohort generation routine until a qualified predictive model is identified, wherein each iteration of the at least one iteration comprises determining one or more predictive cohorts of the plurality of predictive entities for the current iteration based at least in part on each factor score associated with an entity-factor pair, wherein each predictive cohort of the one or more predictive cohorts is associated with a factor range for each predictive factor of the plurality of predictive factors, generating a predictive model for the current iteration based at least in part on the one or more predictive cohorts for the current iteration, performing a predictive inference for the current iteration based at least in part on the predictive model for the current iteration to generate a current iteration prediction for the current iteration, generating a predictive score for the current iteration based at least in part on the current iteration prediction for the current prediction, and determining whether the predictive model for the current iteration is the qualified predictive model based at least in part on the predictive score for the current iteration; and perform the cohort-based predictive data analysis based at least in part on the qualified predictive model to generate a respective final prediction for each predictive entity of the plurality of predictive entities.

In accordance with another aspect, a computer program product is provided. The computer program product may comprise at least one computer-readable storage medium having computer-readable program code portions stored therein, the computer-readable program code portions comprising executable portions configured to receive a plurality of prediction input objects, wherein each of the plurality of prediction input objects is associated with a predictive entity of a plurality of predictive entities; for each entity-factor pair associated with a predictive entity and a predictive factor, generate a factor score indicating a predicted entity-factor relevance of the predictive factor to the corresponding predictive entity based at least in part on the predictive input object associated with the corresponding predictive entity; perform at least one iteration of an iterative cohort generation routine until a qualified predictive model is identified, wherein each iteration of the at least one iteration comprises determining one or more predictive cohorts of the plurality of predictive entities for the current iteration based at least in part on each factor score associated with an entity-factor pair, wherein each predictive cohort of the one or more predictive cohorts is associated with a factor range for each predictive factor of the plurality of predictive factors, generating a predictive model for the current iteration based at least in part on the one or more predictive cohorts for the current iteration, performing a predictive inference for the current iteration based at least in part on the predictive model for the current iteration to generate a current iteration prediction for the current iteration, generating a predictive score for the current iteration based at least in part on the current iteration prediction for the current prediction, and determining whether the predictive model for the current iteration is the qualified predictive model based at least in part on the predictive score for the current iteration; and perform the cohort-based predictive data analysis based at least in part on the qualified predictive model to generate a respective final prediction for each predictive entity of the plurality of predictive entities.

BRIEF DESCRIPTION OF THE DRAWINGS

Figure 1:
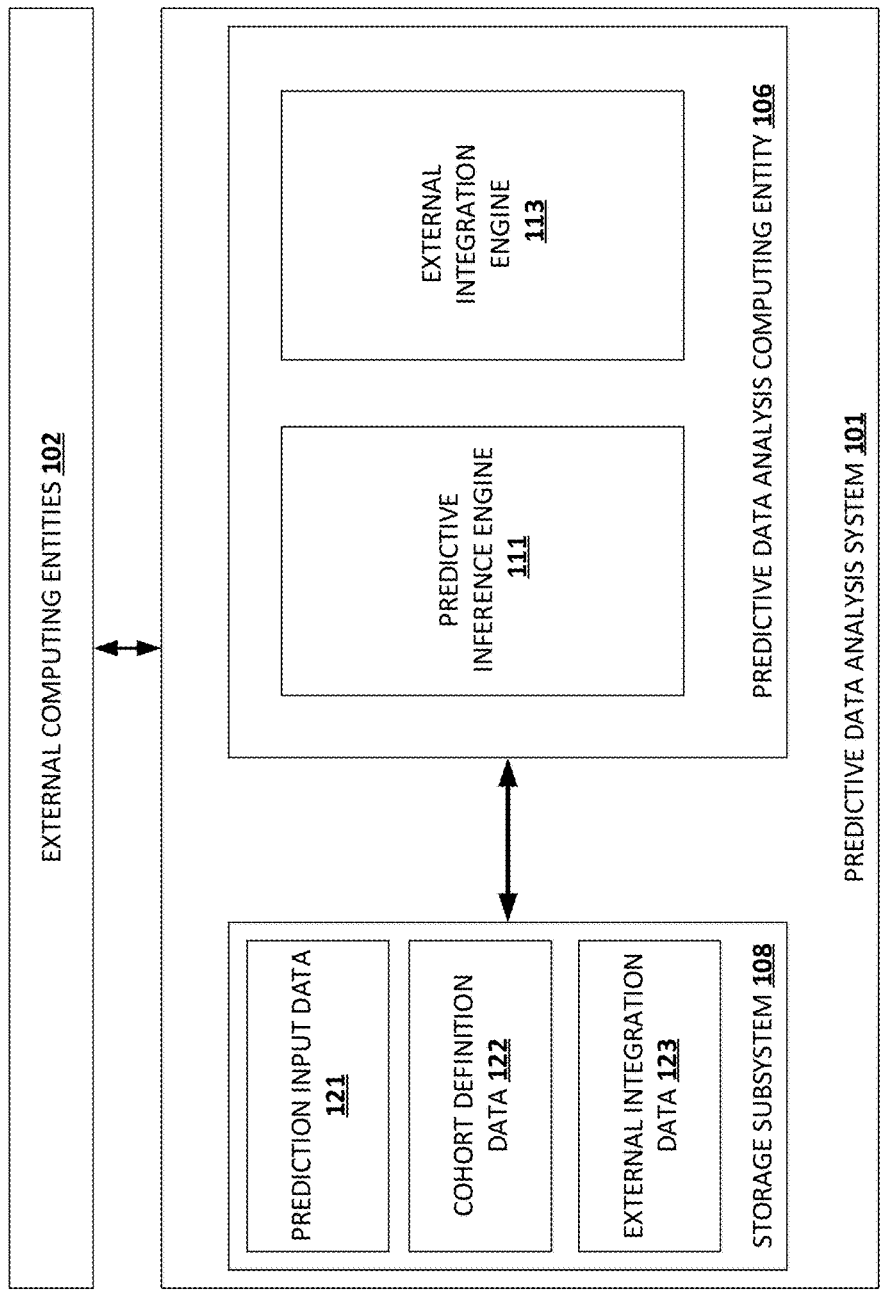

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
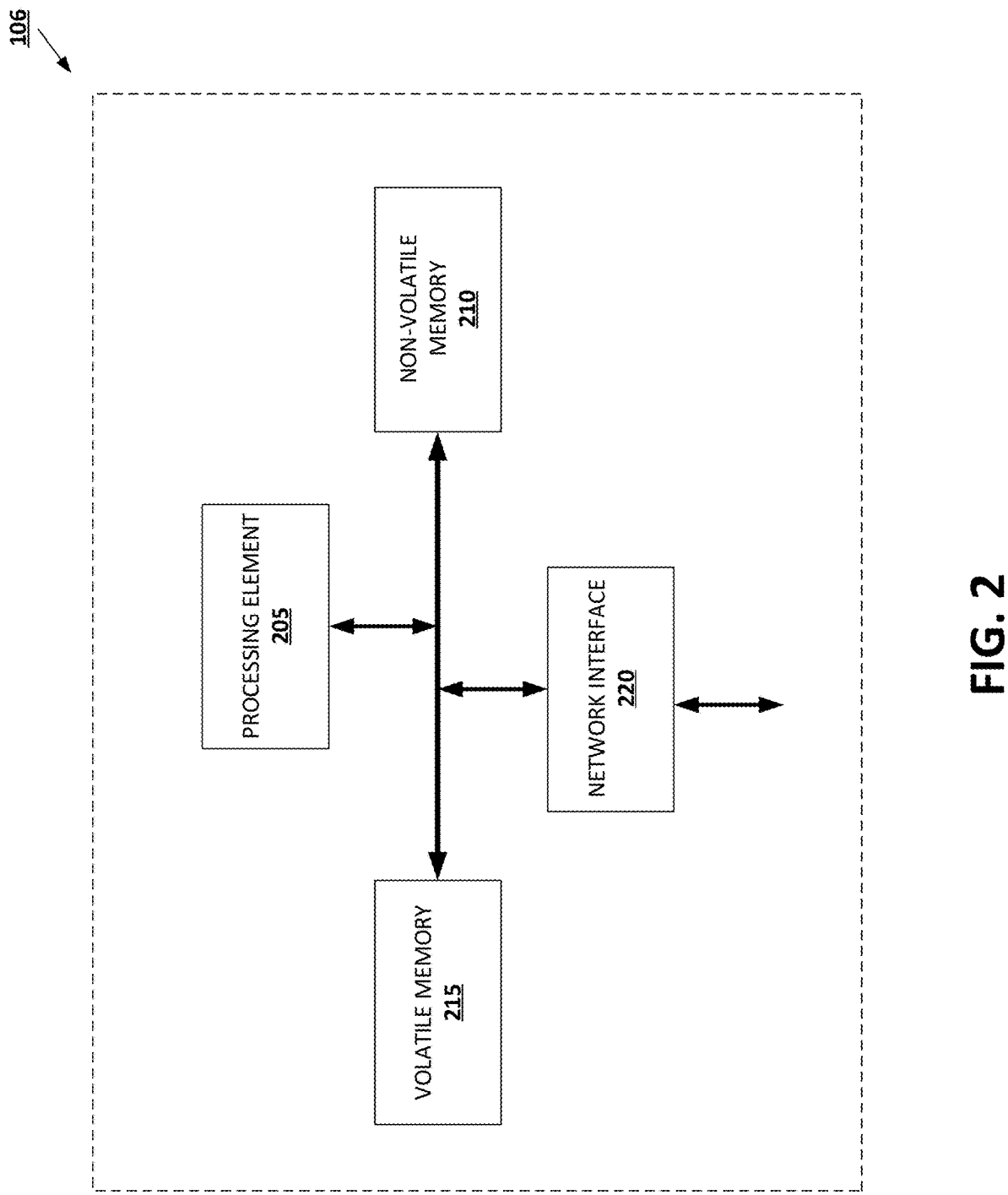

FIG. 2 provides an example predictive data analysis computing entity in accordance with some embodiments discussed herein.

Figure 3:
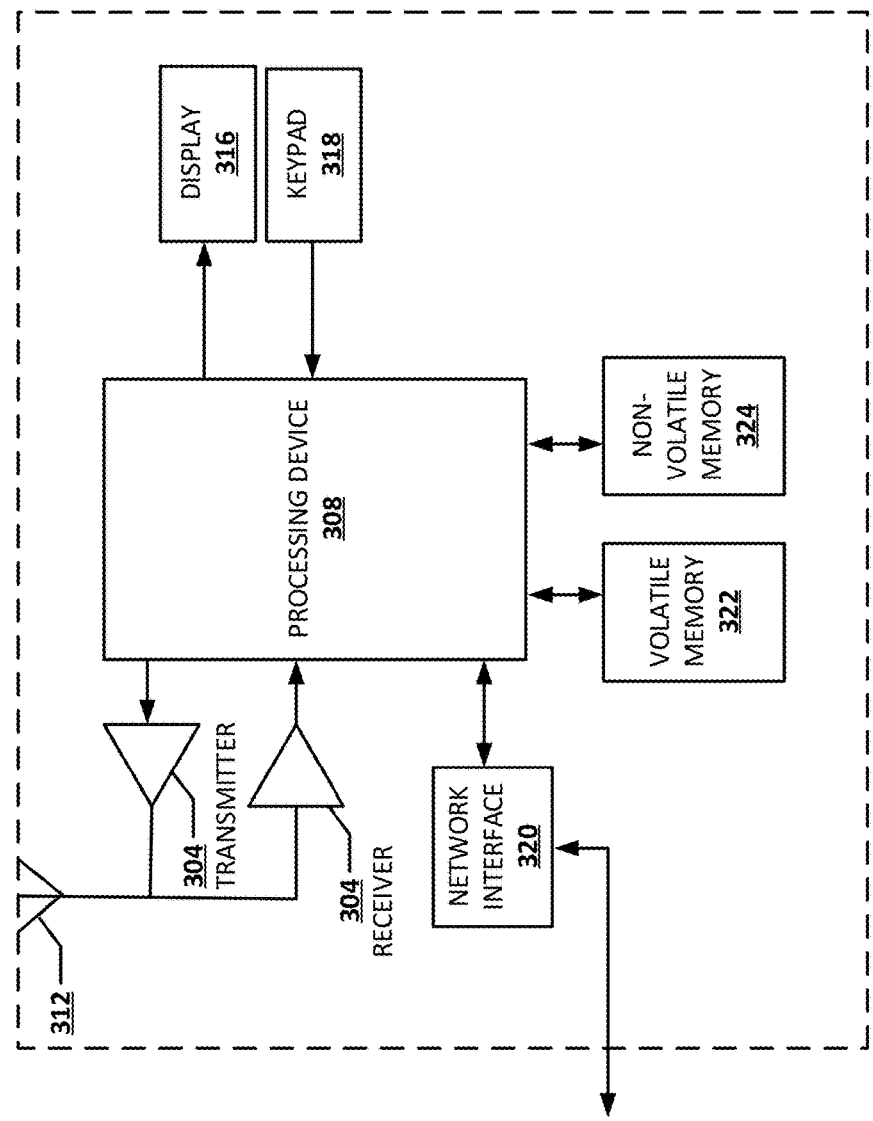

FIG. 3 provides an example external computing entity in accordance with some embodiments discussed herein.

Figure 4:
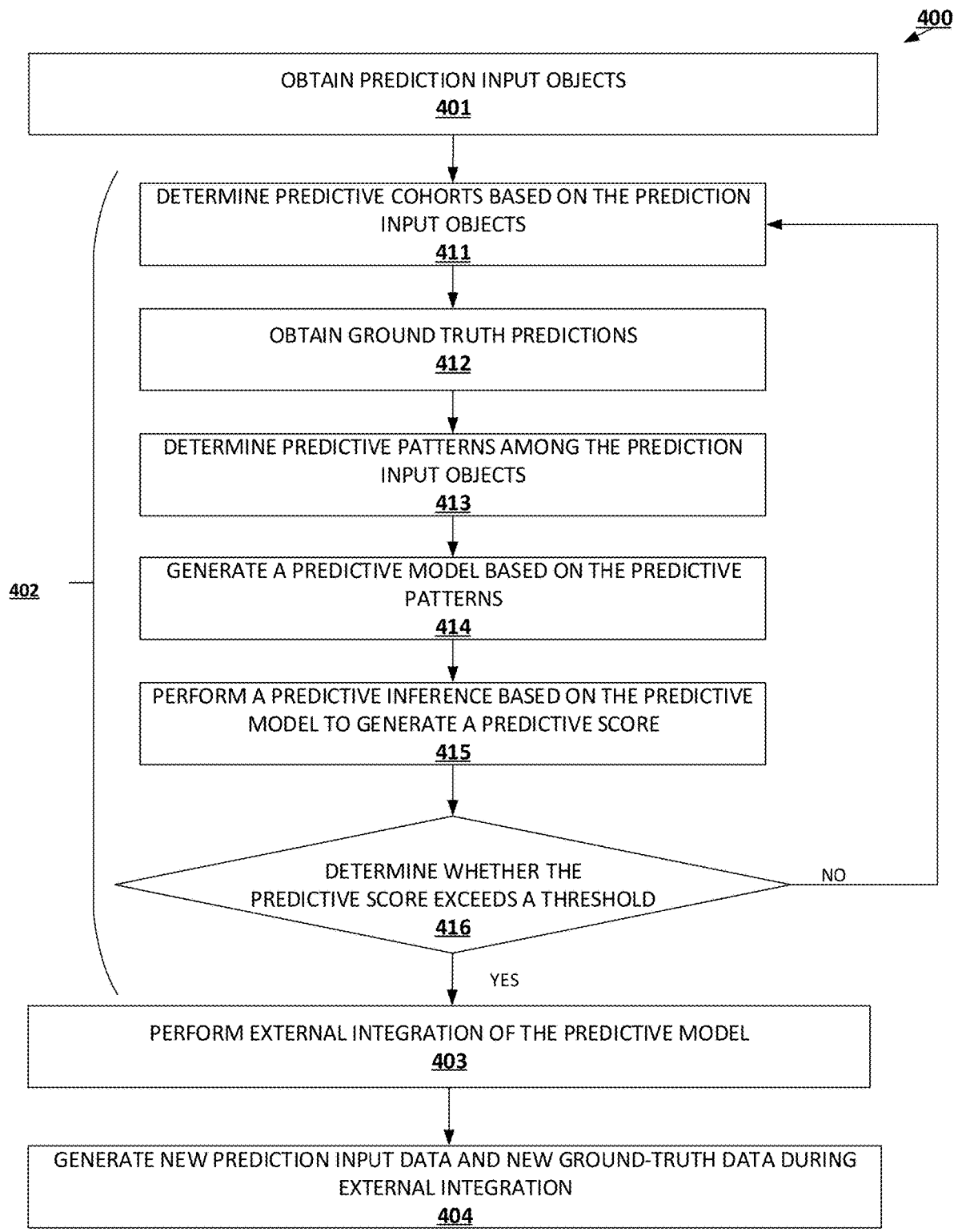

FIG. 4 is a flowchart diagram of an example process for performing cohort-based predictive data analysis in accordance with some embodiments discussed herein.

FIGS. 5A, 5A-1, 5B, and 5B-1 provide operational examples of medical provider factor distributions in accordance with some embodiments discussed herein.

Figure 6:
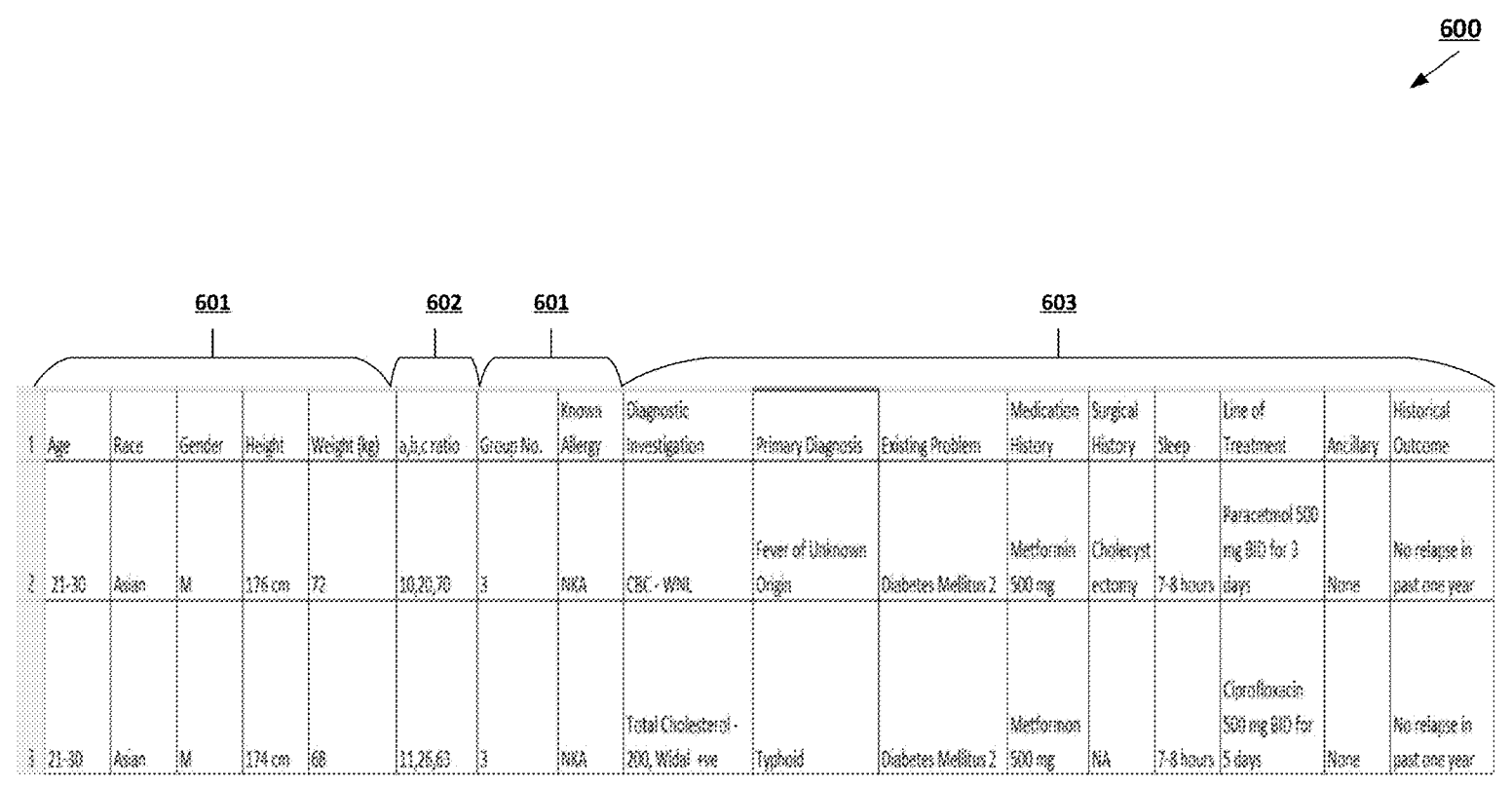

FIG. 6 provides an operational example of two medical prediction information objects in accordance with some embodiments discussed herein.

Figure 7:
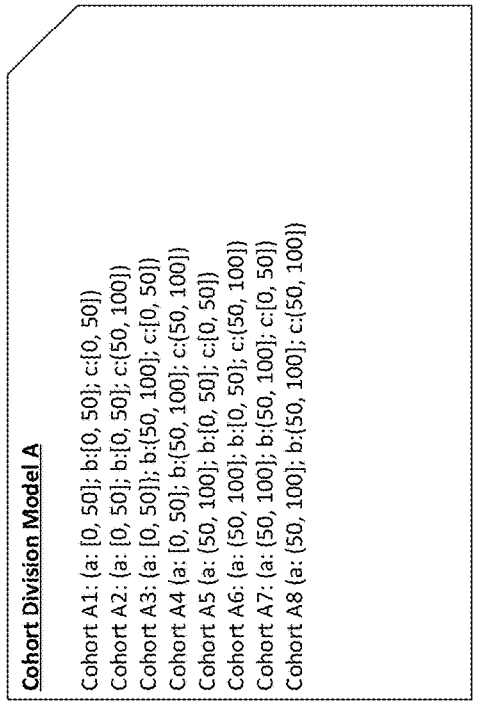

FIG. 7 provides an operational example of various pre-refinement predictive cohorts in accordance with some embodiments discussed herein.

Figure 8:
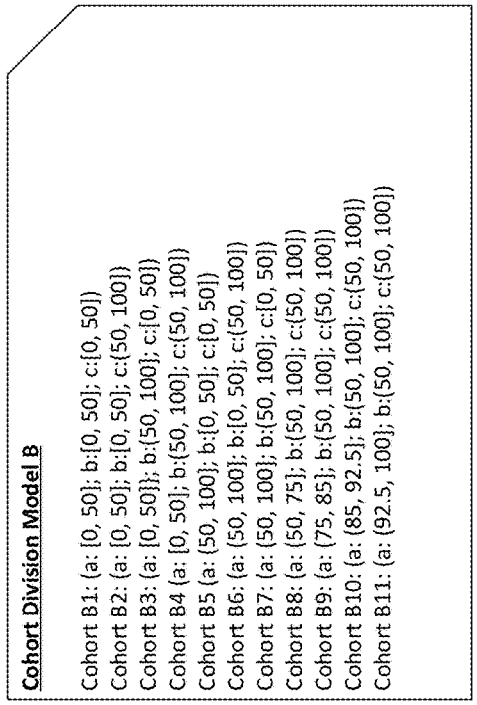

FIG. 8 provides an operational example of various post-refinement predictive cohorts in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview

Discussed herein methods, apparatus, systems, computing devices, computing entities, and/or the like for cohort-based predictive data analysis. As will be recognized, however, the disclosed concepts can be used to perform any type of data analysis, including non-predictive data analysis.

Technical Problems

Various embodiments of the present invention address technical challenges related to predictive data analysis in high-dimensionality and/or highly sparse prediction domains. Examples of high-dimensionality and/or highly sparse domains include many medical prediction domains, such as domains that seek to predict health outcomes based on behavioral and/or phenotypic features of patient predictive entities. In high high-dimensionality and/or highly sparse prediction domains, presence of a large number of input features as well as complex relationships between those input features complicate effective and efficient predictive data analysis. Moreover, absence of sufficient ground-truth data during training undermines the effectiveness of existing dimensionality reduction techniques for reliably and efficiently integrating complexities of input spaces into generated predictive models. As a result, many existing predictive data analysis solutions are ill-suited for predictive data analysis in high-dimensionality and/or highly sparse prediction domains, especially when such prediction domains include complex relationships between various input fields. Accordingly, there is a pressing technical need for effective and efficient data analysis solution that can address unique needs and challenges of high-dimensionality and/or highly sparse domains, such as many medical prediction domains that seek to predict health outcomes based on behavioral and/or phenotypic features of patient predictive entities.

Moreover, various embodiments of the present invention address technical challenges related to developing real-time medical prediction solutions that integrate medical input features (e.g., behavioral and/or phenotype features) to generate medical predictions. In addition to their complex structure, input prediction spaces are also voluminous, thus creating substantial challenges for effective and efficient processing of such data in a manner that integrates various data sources yet produces sufficiently timely predictions. The voluminous nature of medical input spaces creates a challenge for many existing predictive data analysis system that are ill-suited to address the unique needs of such data intensive input spaces. Therefore, many existing predictive data analysis solutions are not able to perform predictive data analysis in medical domains in an effective and efficient manner. As a result, there is a pressing technical need for effective and efficient data analysis solution that can address unique needs and challenges of voluminous and/or data intensive prediction input spaces, such as many medical prediction domains that seek to predict health outcomes based on behavioral and/or phenotypic features of patient predictive entities.

Technical Solutions

Various embodiments of the present invention address technical challenges related to effective and efficient predictive data analysis in high-dimensionality and/or highly cardinality prediction domains by utilizing iterative refinement of predictive cohorts and utilizing refined predictive cohorts to generate predictive models. In some embodiments, if the proposed system determines that the predictive score for a predictive model generated in a particular iteration of an iterative cohort generation routine fails to exceed the predictive score threshold, the system performs a subsequent iteration of the iterative cohort generation routine in order to further refine predictive cohorts. Through this iterative approach, the system can modify modeled interactions between predictive entities over time in order to optimize a predictive utility function, thus in turn achieving a most optimal model of interactions between predictive entities that best describes interrelations between high-dimensionality and/or highly sparse feature data. Thus, by optimizing a cohort division model based on ground-truth feedback, various embodiments of the present invention provide a powerful tool for generating effective predictive models utilized to integrate and describe complex predictive relationships of high-dimensionality and/or highly sparse predictive input spaces.

Moreover, various embodiments of the present invention address technical challenges related to effective and efficient predictive data analysis in high-dimensionality and/or highly cardinality prediction domains by integrating qualified predictive models with external systems and using information gathered from the external systems to dynamically improve predictive models. In some embodiments, after integrating a qualified predictive model with an external system, the proposed system utilizes the external integration with the external system to obtain feature data and/or ground-truth data that can in turn be utilized to further train predictive models and generate optimized divisions of predictive entities into various predictive cohorts. By utilizing new feature data and/or new ground-truth data to further train predictive models and generate optimized divisions of predictive entities into various predictive cohorts, various embodiments of the present invention enable dynamic refinement and improvement of the predictive models over time through interactions with real-world sources of information. This dynamic refinement and improvement of predictive models, rendered feasible in part because of the training efficiency and reusability of the cohort-based techniques utilized to generate predictive models, enables generation of effective and reliable predictive models that are responsive to real-world changes in data repositories and can thus perform effective and efficient on-demand and real-time predictive data analysis. Such techniques for effective and efficient on-demand and real-time predictive data analysis are especially useful for data intensive domains as well as domains associated with high-dimensionality and/or high cardinality input spaces, such as various medical prediction domains.

Through utilizing iterative refinement of cohorts and/or dynamic training of predictive models over time based on emerging data repositories, various embodiments of the present invention generate highly effective and reliable predictive models that can be utilized to perform various highly critical predictive task. In some embodiments, the proposed system can utilize the qualified predictive model to perform one or more prediction-based actions based on one or more inferred predictions of the qualified predictive model. For example, the system can utilize the qualified predictive model to generate one or more medical alerts, e.g., one or more alerts to medical provider user profiles and/or one or more alerts to patient user profiles. As another example, the system can utilize the qualified predictive model to schedule one or more medical appointments. As a further example, the system can utilize the qualified predictive model to perform one or more operational load balancing systems, e.g., perform operational load balancing actions for a hospital computer system, perform operational load balancing for a provider utilization model associated with a hospital system, perform operational load balancing for a pharmacy institutions based on patient health projections. As yet another example, the system can utilize the qualified predictive model to generate one or more targeted medical recommendations and/or targeted action recommendations, such as one or more diet plans, one or more drug recommendations, etc.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

The architecture 100 includes one or more external computing entities 102 that interact with a predictive data analysis system 101 via a communication network (not shown). The predictive data analysis system 101 includes a storage subsystem 108 and a predictive data analysis computing entity 106. Each computing entity, computing subsystem, and/or computing system in the architecture 100 may include any suitable network server and/or other type of processing device. The communication network may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

In some embodiments, the architecture 100 is configured to enable the external computing entities 102 to provide prediction inputs to the predictive data analysis system 101 and, in response, receive predictions generated based on the prediction inputs. For example, a particular external computing entity 102 may provide a request for a health-outcome-related prediction for a patient, where the request may include data associated with the patient (e.g., personal attribute data associated with the patient, medical codes associated with the medical history of the patient, etc.). The predictive data analysis system 101 is configured to generate the requested health-outcome-related prediction and provide the generated health-outcome-related prediction to the particular external computing entity 102. In some embodiments, the external computing entity 102 may be a computing entity associated with a medical provider institution and/or a health insurance provider institution.

The predictive data analysis computing entity 106 includes a predictive inference engine 111 configured to perform predictive inferences based on prediction inputs and ground-truth predictions in order to generate a qualified predictive model. The predictive inference engine 111 may obtain prediction inputs and ground-truth predictions from at least one of one or more external computing entities 102 and the storage subsystem 108. The predictive data analysis computing entity 106 further includes an external integration engine 113 configured to integrate a qualified predictive mode generated by the predictive inference engine 111 with one or more external systems, e.g., one or more external systems each associated with an external computing entity. Examples of external systems includes emergency medical record (EMR) systems and medical point-of-care systems.

The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

The storage subsystem 108 may include prediction input data 121, cohort definition data 122 used by the predictive inference engine 111 to generate predictive cohorts which are in turn used to generate predictive models, and external integration data 123 utilized by the external integration engine 113 to integrate a qualified predictive model with one or more external systems. For example, external integration data 123 may include configuration data used by the external integration engine 113 to integrate a qualified predictive model with an external system based on one or more properties of the particular qualified predictive model and/or one or more properties of the particular external system.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1X (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, respectively.

The signals provided to and received from the transmitter 304 and the receiver 306, respectively, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1xRTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MIMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. Exemplary System Operation

Various embodiments of the present invention address technical challenges related to effective and efficient predictive data analysis in high-dimensionality and/or highly cardinality prediction domains by utilizing iterative refinement of predictive cohorts and utilizing refined predictive cohorts to generate predictive models. Moreover, various embodiments of the present invention address technical challenges related to effective and efficient predictive data analysis in high-dimensionality and/or highly cardinality prediction domains by integrating qualified predictive models with external systems and using information gathered from the external systems to dynamically improve predictive models. Through utilizing iterative refinement of cohorts and/or dynamic training of predictive models over time based on emerging data repositories, various embodiments of the present invention generate highly effective and reliable predictive models that can be utilized to perform various highly critical predictive task.

Cohort-Based Predictive Data Analysis

FIG. 4 is a flowchart diagram of an example process 400 for performing cohort-based predictive data analysis. Through the various steps/operations of process 400, the predictive data analysis computing entity 106 of the predictive data analysis system 101 can perform predictive data analysis by iterative refinement of predictive cohorts in a manner that facilitates predictive data analysis in high-dimensionality and/or highly sparse input spaces, such as input spaces associated with health-related feature data.

The process 400 begins at step/operation 401 when the predictive inference engine 111 of the predictive data analysis computing entity 106 obtains one or more prediction input objects. In some embodiments, the predictive inference engine 111 retrieves prediction input data 121 from the storage subsystem 108 and generates the one or more prediction input objects from the retrieved prediction input data 121. In some embodiments, at least some of the prediction input data 121 and/or at least some of the prediction input objects are stored as structured data (e.g., in a Structured Query Language Format (SQL)) and/or as formatted files (e.g., files formatted according to a JavaScript Object Notation (JSON) format). In some embodiments, at least some of the prediction input data 121 and/or at least some of the prediction input objects are generated based on data provided by an external computing entity 102, such as data provided by an end user of an external computing entity 102.

For example, at least some of the prediction input data 121 and/or at least some of the prediction input objects may be generated based on patient survey data provided by a patient profile associated with a patient end user of an external computing entity 102 configured to enable patient end users to interact with a medical system. As another example, at least some of the prediction input data 121 and/or at least some of the prediction input objects may be generated based on medical provider survey data provided by a medical provider profile associated with a medical provider end user of an external computing entity 102 configured to enable medical provider end users to interact with a medical system. As yet another example, at least some of the prediction input data 121 and/or at least some of the prediction input objects may be generated based on medical claims feature data provided by a medical provider profile associated with a medical provider end user of an external computing entity 102 configured to enable medical provider end users to interact with a medical system. As a further example, at least some of the prediction input data 121 and/or at least some of the prediction input objects may be generated based on medical notes feature data provided by a medical provider profile associated with a medical provider end user of an external computing entity 102 configured to enable medical provider end users to interact with a medical system.

In some embodiments, each prediction input object includes one or more prediction features and/or is associated with a predictive entity. For example, a prediction input object may include one or more health-related prediction features associated with a patient predictive entity for the prediction input object. As another example, a prediction input object may include one or more prediction features that identify the predictive entity associated with the prediction input object, e.g., a patient identifier for a patient predictive entity associated with the prediction input object. As yet another example, a prediction input object may include one or more phenotype-related prediction features associated with a patient predictive entity. As a further example, a prediction input object may include one or more behavior-related prediction features associated with a patient predictive entity.

At step/operation 402, the predictive inference engine 111 performs a number of iterations of an iterative cohort generation routine. In some embodiments, by performing the number of iterations of the iterative cohort generation routine, the predictive inference engine 111 seeks to identify a manner of dividing the predictive entities associated with the predictive input objects obtained in step/operation 401 that achieves a threshold level of predictive accuracy when used to perform cohort-based predictive data analysis system. Thus, in some embodiments, the predictive inference engine 111 iteratively refines division of predictive input objects into predictive cohorts in a manner configured to optimize the predictive inference performed using the predictive cohorts.

In some embodiments, a particular iteration of the iterative cohort generation routine comprises performing steps/operations 411-416. At step/operation 411 of the iterative cohort generation routine, the predictive inference engine 111 determines predictive cohorts based on prediction input objects. In some embodiments, if the particular iteration of the iterative cohort generation routine is an initial iteration of the iterative cohort generation routine, the predictive inference engine 111 generates one or more cohorts based on one or more cohort definition parameters for a particular predictive data analysis task (e.g., one or more cohort definition parameters retrieved as part of the cohort definition data 122 of the storage subsystem 108). In some embodiments, if the particular iteration of the iterative cohort generation routine is a post-initial iteration of the iterative cohort generation routine that occurs after the initial iteration of the iterative cohort generation routine, the predictive inference engine 111 generates one or more cohorts based on at least one of: (i) on one or more cohort definition parameters for a particular predictive data analysis task (e.g., one or more cohort definition parameters retrieved as part of the cohort definition data 122 of the storage subsystem 108) and (ii) inferences drawn from predictive scores of one or more iterations of the iterative cohort generation routine prior to the particular iteration. In some of those embodiments, the predictive inference engine 111 may determine, based on a predictive score of an immediately precedent iteration for the particular iteration, that the predictive inference engine 111 should further divide ranges of one or more predictive factors to generate new predictive cohorts and limit corresponding ranges of existing predictive cohorts. For example, if the predictive score of an nth iteration associated with three predictive cohorts fails to satisfy a prediction threshold, the predictive inference engine 111 may perform the n+1th iteration with more than three predictive cohorts by reducing ranges of predictive factors used to generate predictive cohorts.

In some embodiments, the predictive inference engine 111 determines the predictive cohorts based on one or more predictive factors. For example, the predictive inference engine 111 may generate, for each entity-factor pair of multiple entity-factor pairs that is associated with a predictive entity of a plurality of predictive entities and a predictive factor of a plurality of predictive factors, a factor score indicating a predicted entity-factor relevance of the predictive factor to the predictive entity based at least in part on the predictive input object associated with the predictive entity. The predictive inference engine 111 may further identify range of each predictive factor and define the predictive cohorts based on subranges of the predictive factors. For example, if the predictive factors include a first predictive factor PF1 having a range [1, 100], a second predictive factor PF2 having a range [YES, NO], and a third predictive factor PF3 having a range [0, 1], the predictive inference engine 111 may define the following predictive cohorts: a first predictive cohort associated with subrange [1, 50] for PF1, subrange [YES] for PF2, and subrange [0.5, 1] for PF3; a second predictive cohort associated with subrange (50, 100] for PF1, subrange [YES] for PF2, and subrange [0.5, 1] for PF3; a third predictive cohort associated with subrange [1, 50] for PF1, subrange [NO] for PF2, and subrange [0.5, 1] for PF3; a fourth predictive cohort associated with subrange [1, 50] for PF1, subrange [NO] for PF2, and subrange [0, 0.5) for PF3; etc. (where [a, b] indicates a subrange that is open on both sides, (a, b] indicates a subrange that is closed on the left but open on the right, [a, b) indicates a subrange that is closed on the right but open on the left, and (a, b) indicates a subrange that is closed on both sides).

In some embodiments, at least some of the predictive factors may be determined based on predictive parameter values for one or more predictive parameters. Examples of predictive parameters include medical predictive parameters, such as predictive parameters determined from traditional Indian medicine categorizations of medical qualities and/or behavioral qualities of individuals. Examples of distribution of medical predictive factors over various medical predictive parameters are depicted in the medical predictive factor distribution 510 and the medical predictive factor distribution 560. As depicted in the medical predictive factor distribution 510 of FIGS. 5A and 5A-1 and the medical predictive factor distribution 560 of FIGS. 5B and 5B-1, each medical predictive factor a, b, and c corresponds to designated medical parameter values for each of at least fifty five medical parameters. For example, as depicted in the medical predictive factor distribution 510, the medical predictive factor a is associated with absence of a contentment predictive medical parameter, lack of a will power predictive medical parameter, short term nature of a planning predictive medical parameter. As another example, as depicted in the medical predictive factor distribution 560, the medical predictive factor c is associated with strong nature of a strength predictive medical parameter, largeness of a forehead predictive medical parameter, heaviness of a weight predictive medical parameter, and slowness of a pulse predictive medical parameter. As yet another example, as depicted in the medical predictive factor distribution 510, the medical predictive factor b is associated with coldness of a climate and food medical predictive parameter, low nature of an ability to tolerate exertion medical predictive parameter, moderate nature of a gait medical predictive parameter, and moderate nature of an energy medical predictive parameter. As a further example, as depicted in the medical predictive factor distribution 560, the medical predictive factor a is associated with darkness of a color medical predictive parameter, smallness of a shoulder and chest medical predictive parameter, thirsty nature of a thirst predictive parameter, and scantiness of a semen medical predictive parameter.

The predictive inference engine 111 may utilize predictive parameters for multiple predictive parameters to determine factor scores for predictive factors for a predictive entity. In some embodiments, the predictive inference engine 111 may aggregate the number of predictive parameters whose corresponding predictive parameter values for a particular predictive entity is associated with a particular predictive factor to determine one or more predictive scores for the particular predictive entity. For example, if a particular patient predictive entity is associated with the predictive parameter values {contentment: absent; will power: fair; friendship: many and lasting relationships; memory: fair; planning: short term; gait: moderate}, the predictive inference engine 111 may determine the following factor score for the particular patient based on the medical predictive factor distribution 510 of FIGS. 5A and 5A-1: a factor score of two for the predictive factor a (based on positive values for the contentment medical predictive parameter and the planning medical predictive parameter), a factor score of five for the predictive factor b (based on positive values for the contentment medical predictive parameter, the will power medical predictive parameter, the memory medical predictive parameter, the planning medical predictive parameter, and the gait medical predictive parameter) and a factor score of one for the predictive factor c (based on a positive value for the memory medical predictive parameter).

In some embodiments, the predictive inference engine 111 may first apply a parameter weighting score for a particular predictive parameter to each positive predictive parameter value associated with the particular predictive parameter before aggregating the positive predictive parameter values to generate factor scores. For example, in the example described in the previous paragraph, given the parameter weighting scores {contentment: 0.5; will power: 0.7; friendship: 0.9; memory: 0.1; planning: 0.3; gait: 0.4}, the predictive inference engine 111 may determine the following factor score for the particular patient based on the medical predictive factor distribution 510 of FIGS. 5A and 5A-1 and the noted parameter weighting scores: a factor score of 0.8 for the predictive factor a (based on positive values for the contentment medical predictive parameter having a 0.5 parameter weighting score and the planning medical predictive parameter having a 0.3 parameter weighting score, thus resulting in a factor score of 0.5+0.3=0.8), a factor score of 2.0 for the predictive factor b (based on positive values for the contentment medical predictive parameter having a 0.5 parameter weighting score, the will power medical predictive parameter having a 0.7 parameter weighting score, the memory medical predictive parameter having a 0.1 parameter weighting score, the planning medical predictive parameter having a 0.3 parameter weighting score, and the gait medical predictive parameter having a 0.4 parameter weighting score, thus resulting in a predictive factor score of 0.5+0.7+0.1+0.3+0.4=2.0) and a factor score of 0.9 for the predictive factor c (based on a positive value for the memory medical predictive parameter having a 0.9 parameter weighting score, thus resulting in a factor score of 0.9). In some embodiments, at least some of the parameter weighting scores for the predictive parameter values are stored as part of the cohort definition data 122 on the storage subsystem 108.

In some embodiments, the predictive inference engine 111 determines predictive cohorts based on subranges within the ranges of predictive factors. In some embodiments, the predictive inference engine 111 defines each predictive cohorts based on a subrange for each of at least some of the predictive factors. For example, given the predictive factors a, b, and c each having a range [0, 1], the predictive inference engine may generate the following predictive cohorts: a first cohort associated with a subrange [0, 0.5] for the predictive factor a, a subrange [0, 0.5] for the predictive factor b, and a subrange [0, 0.5] for the predictive factor c; a second cohort associated with a subrange [0, 0.5] for the predictive factor a, a subrange [0, 0.5] for the predictive factor b, and a subrange (0.5, 1] for the predictive factor c; a third cohort associated with a subrange [0, 0.5] for the predictive factor a, a subrange (0.5, 1] for the predictive factor b, and a subrange [0, 0.5] for the predictive factor c; a fourth cohort associated with a subrange [0, 0.5] for the predictive factor a, a subrange (0.5, 1] for the predictive factor b, and a subrange [0, 0.5] for the predictive factor c; etc. (where [a, b] indicates a subrange that is open on both sides, (a, b] indicates a subrange that is closed on the left but open on the right, [a, b) indicates a subrange that is closed on the right but open on the left, and (a, b) indicates a subrange that is closed on both sides).

Examples of cohort division models based on factor scores for predictive factors are depicted in the cohort division model A 700 of FIG. 7 and the cohort division model B 800 of FIG. 8. For example, the cohort division model A 700 of FIG. 7 defines the following eight predictive cohorts based on subranges of factor scores for predictive factors a, b, and c: predictive cohort A1 associated with subrange [0, 50] for predictive factor a, subrange [0, 50] for predictive factor b, and subrange [0, 50] for predictive factor c; predictive cohort A2 associated with subrange [0, 50] for predictive factor a, subrange [0, 50] for predictive factor b, and subrange (50, 100] for predictive factor c; predictive cohort A3 associated with subrange [0, 50] for predictive factor a, subrange (50, 100] for predictive factor b, and subrange [0, 50] for predictive factor c; predictive cohort A4 associated with subrange [0, 50] for predictive factor a, subrange (50, 100] for predictive factor b, and subrange (50, 100] for predictive factor c; predictive cohort A5 associated with subrange (50, 100] for predictive factor a, subrange [0, 50] for predictive factor b, and subrange [0, 50] for predictive factor c; predictive cohort A6 associated with subrange (50, 100] for predictive factor a, subrange [0, 50] for predictive factor b, and subrange (50, 100] for predictive factor c; predictive cohort A7 associated with subrange (50, 100] for predictive factor a, subrange (50, 100] for predictive factor b, and subrange [0, 50] for predictive factor c; and predictive cohort A8 associated with subrange (50, 100] for predictive factor a, subrange (50, 100] for predictive factor b, and subrange (50, 100] for predictive factor c.

Moreover, the cohort division model B 800 of FIG. 8 defines the following eleven predictive cohorts based on subranges of factor scores for predictive factors a, b, and c: predictive cohort B1 associated with subrange [0, 50] for predictive factor a, subrange [0, 50] for predictive factor b, and subrange [0, 50] for predictive factor c; predictive cohort B2 associated with subrange [0, 50] for predictive factor a, subrange [0, 50] for predictive factor b, and subrange (50, 100] for predictive factor c; predictive cohort B 3 associated with subrange [0, 50] for predictive factor a, subrange (50, 100] for predictive factor b, and subrange [0, 50] for predictive factor c; predictive cohort B4 associated with subrange [0, 50] for predictive factor a, subrange (50, 100] for predictive factor b, and subrange (50, 100] for predictive factor c; predictive cohort B5 associated with subrange (50, 100] for predictive factor a, subrange [0, 50] for predictive factor b, and subrange [0, 50] for predictive factor c; predictive cohort B6 associated with subrange (50, 100] for predictive factor a, subrange [0, 50] for predictive factor b, and subrange (50, 100] for predictive factor c; predictive cohort B7 associated with subrange (50, 100] for predictive factor a, subrange (50, 100] for predictive factor b, and subrange [0, 50] for predictive factor c; predictive cohort B8 associated with subrange (50, 75] for predictive factor a, subrange (50, 100] for predictive factor b, and subrange (50, 100] for predictive factor c; predictive cohort B9 associated with subrange (75, 85] for predictive factor a, subrange (50, 100] for predictive factor b, and subrange (50, 100] for predictive factor c; predictive cohort B10 associated with subrange (85, 92.5] for predictive factor a, subrange (50, 100] for predictive factor b, and subrange (50, 100] for predictive factor c; and predictive cohort B11 associated with subrange (92.5, 100] for predictive factor a, subrange (50, 100] for predictive factor b, and subrange (50, 100] for predictive factor c.

In some embodiments, by generating predictive cohorts based on predictive factors, the predictive inference engine 111 can accomplish at least one of the following two objectives: (i) reducing dimensionality of data through modeling and iteratively refining inter-relations between the various predictive parameters that define the input space for predictive data analysis; and (ii) providing domain-specific information about iterations of predictive parameters when such domain-specific information may not be properly captured by numeric predictive data analysis models. In some embodiments, by reducing dimensionality of data through modeling and iteratively refining inter-relations between the various predictive parameters that define the input space for predictive data analysis, the predictive inference engine 111 can generate more accurate predictions and can substantially increase both training efficiency and inference efficiency of predictive data analysis models. In some embodiments, by providing domain-specific information about iterations of predictive parameters when such domain-specific information may not be properly captured by numeric predictive data analysis models, the predictive inference engine 111 can improve accuracy and reliability of predictive data analysis as well as reduce training efficiency of predictive data analysis solutions utilized in high-dimensionality and/or highly sparse input spaces.

Returning to FIG. 4, at step/operation 412 of the particular iteration of the iterative cohort generation routine, the predictive inference engine 111 obtains ground-truth predictions. In some embodiments, the predictive inference engine 111 obtains ground-truth predictions about at least some of the predictive entities associated with the prediction input objects obtained in step/operation 401. Examples of ground-truth predictions include real-world facts associated with the predictive entities, such as diagnostic or health-outcome information associated with particular predictive entity. In some embodiments, the predictive inference engine 111 obtains the diagnostic or health-outcome information from an external computing entity 102, such as an external computing entity 102 associated with a medical provider institution and/or a health insurance provider institution.

At step/operation 413 of the particular iteration of the iterative cohort generation routine, the predictive inference engine 111 determines predictive patterns among the prediction objects. For example, the predictive inference engine 111 may determine predictive patterns based on correspondence of predictive cohorts generated in step/operation 411 and ground-truth predictions obtained in step/operation 412. In some embodiments, the predictive patterns describe at least one shared feature associated with ground-truth predictions associated with predictive entities in a particular predictive cohort. For example, a particular predictive pattern may describe that ground-truth predictions associated with patient predictive entities that belong to a first predictive cohort indicate a higher risk of developing cancer. As another example, a particular predictive pattern may describe that ground-truth predictions associated with patient predictive entities that belong to a second predictive cohort indicate higher weight loss patterns. As a further example, a particular predictive pattern may describe that ground-truth predictions associated with patient predictive entities that belong to a third predictive cohort indicate developing ovarian cancer at a younger age.

At step/operation 414 of the particular iteration of the iterative cohort generation routine, the predictive inference engine 111 generates a predictive model based on the predictive patterns. In some embodiments, the predictive inference engine 111 generates a predictive model that relates predictive patterns determined in step/operation 413 to predicted outcomes, where the predictive model may be defined by one or more predictive model parameters that each relate an aspect of the predictive patterns to particular predictions. In some embodiments, the predictive inference engine 111 may generate a predictive model that relates correspondence of prediction input data associated with a particular predictive entity to a prediction for the particular predictive entity. For example, the generated predictive model may relate health feature data for a patient predictive entity to a predicted health outcome for the patient predictive entity.

In some embodiments, the predictive inference engine 111 generates the predictive model using a training algorithm. Examples of suitable training algorithms include algorithms that optimize an error function and/or a utility function for a predictive model, such as a training algorithm that use at least one of gradient descent, gradient descent with backpropagation, and/or gradient descent with backpropagation over time. In some embodiments, the predictive inference engine 111 stores the generated predictive model in the storage subsystem 108 and/or provides the generated predictive model to an external computing entity 102, such as an external computing entity 102 associated with a medical provider institution and/or a health insurance provider institution.

In some embodiments, to generate the predictive model, the predictive inference engine 111 utilizes one or more training data objects, such as the training data objects depicted in the training data object set 600 of FIG. 6. As depicted in the training data object set 600 of FIG. 6, each patient predictive entity of two predictive data entities is associated with prediction input features 601 (e.g., prediction input features corresponding to age, race, gender, height, weight, group on, known allergies, etc.). Furthermore, each patient predictive entity is also associated with three prediction factors 602 each associated with a prediction factor of the three prediction factors a, b, and c. Moreover, each patient predictive entity may be associated with one or more ground-truth information 603 (e.g., ground-truth information corresponding to diagnostic investigation type, primary diagnosis information, existing problem identification, medical history, surgical history, sleep pattern, line of treatment, ancillary diagnostic information, historical outcomes, etc.).

At step/operation 415 of the particular iteration of the iterative cohort generation routine, the predictive inference engine 111 performs a predictive inference based on the predictive model generated in step/operation 414 to generate a predictive score for the predictive model. In some embodiments, the predictive inference engine 111 performs predictions using the predictive model and based on the prediction inputs for at least some of the predictive entities whose corresponding ground-truth predictions were obtained in step/operation 412 to generate inferred predictions for the noted predictive entities. In some of those embodiments, the predictive inference engine 111 compares the inferred predictions for the noted predictive entities and the ground-truth predictions for the noted predictive entities to generate the predictive score for the predictive model. For example, the predictive inference engine 111 may generate the predictive score for the predictive model based on a measure of statistical distribution (e.g., a mean, median, mode, etc.) of deviations between inferred predictions and ground-truth predictions. As another example, the predictive inference engine 111 may generate an error function based on deviations between inferred predictions and ground-truth predictions and generate the predictive score for the predictive model based on at least one property of the generated error function. In some embodiments, the predictive inference engine 111 utilizes a first portion (e.g., three-fourth) of the ground-truth predictions obtained in step/operation 412 for generating the predictive model in step/operation 414 and a remaining second portion (e.g., one-fourth) of the ground-truth predictions obtained in step/operation 412 for determining the predictive score for the generated predictive model in step/operation 415.

At step/operation 416 of the particular iteration of the iterative cohort generation routine, the predictive inference engine 111 determines whether the predictive score exceeds a predictive score threshold. In some embodiments, the predictive score threshold indicates a desire degree of a predictive accuracy for a predictive model that indicates that the cohort division model used to generate the predictive model has been sufficiently refined. In some embodiments, the predictive score thresholds for various predictive data analysis tasks and/or various batches of prediction input data may be different. In some embodiments, the predictive score threshold is stored as part of the cohort definition data 122 on the storage subsystem 108.

In some embodiments, if the predictive inference engine 111 determines that the predictive score for a predictive model generated in a particular iteration of the iterative cohort generation routine fails to exceed the predictive score threshold, the predictive inference engine 111 performs a subsequent iteration of the iterative cohort generation routine in order to further refine predictive cohorts. Through this iterative approach, the predictive inference engine 111 can modify modeled interactions between predictive entities over time in order to optimize a predictive utility function, thus in turn achieving a most optimal model of interactions between predictive entities that best describes interrelations between high-dimensionality and/or highly sparse feature data. Thus, by optimizing a cohort division model based on ground-truth feedback, various embodiments of the present invention provide a powerful tool for generating effective predictive models utilized to integrate and describe complex predictive relationships of high-dimensionality and/or highly sparse predictive input spaces.

The cohort division models A 700 and B 800 of FIGS. 7-8 provide an operational example of iterative refinement of cohort division model through at least two iterations of an iterative cohort generation routine. In particular, cohort division model B 800 may be generated by dividing cohort A8 of the cohort division model A 700 into four cohorts B8-B11. More specifically, to generate cohorts B8-B11, the predictive inference engine 111 has broken the subrange of cohort A8 for predictive component a (e.g., the subrange (50, 100]) into four subranges: subrange (50, 75] for predictive cohort B8, subrange (75, 85] for predictive cohort B9, subrange (85, 92.5] for predictive cohort B10, and subrange (92.5, 100] for predictive cohort B11. Although the operational example depicted using FIGS. 7-8 breaks one subrange associated with one initial predictive cohort into four refined predictive cohorts, a person of ordinary skill in the art will recognize that any refinement of predictive cohorts may break any one or more subranges associated with any one or more initial predictive cohorts into any number of refined predictive cohorts. Moreover, although the operational example depicted in FIGS. 7-8 show one iterative refinement, one of ordinary skill in the art will recognize that any number of refinements of predictive cohorts may be performed until a predictive model generated based cohort refinements achieves a predictive score that exceeds a threshold predictive score and/or satisfies a threshold predictive score condition.

External Integration of Cohort-Based Predictive Models

In some embodiments, if the predictive inference engine 111 determines that the predictive score for a predictive model generated in a particular iteration of the iterative cohort generation routine exceeds the predictive score threshold, the external integration engine 113 of the predictive data analysis computing entity 106 proceeds to perform steps/operations 403-404 of process 400. In some embodiments, in response to a determination by the predictive inference engine 111 that the predictive score for a predictive model generated in a particular iteration of the iterative cohort generation routine exceeds the predictive score threshold, the predictive inference engine 111 determines that the predictive model is a qualified predictive model and the external integration engine 113 proceeds to perform steps/operation 403-404 based on the qualified predictive model.

At step/operation 403, the external integration engine 113 performs external integration of the predictive model. In some embodiments, in response to a determination by the predictive inference engine 111 that the predictive score for a predictive model generated in a particular iteration of the iterative cohort generation routine exceeds the predictive score threshold, the predictive inference engine 111 determines that the predictive model is a qualified predictive model and the external integration engine 113 proceeds to integrate the qualified predictive model with one or more external systems.

Examples of external systems include EMR systems and point-of-care systems for medical care institutions. In some embodiments, to perform integration of the qualified predictive model with an external system, the external integration engine 113 maps one or more inputs and/or one or more outputs of the qualified predictive model to one or more application programming interface (API) calls of the external system. For example, the external integration engine 113 may one or more inputs and/or one or more outputs of the qualified predictive model to one or more API calls of an EMR system and/or a point-of-care system. In some embodiments, to integrate the qualified predictive model with an external system, the external integration engine 113 utilizes configuration data related to integrating the particular predictive model with the particular external data. The mentioned configuration data may be retrieved by the external integration engine 113 as part of the external integration data 123 stored on the storage subsystem. In some embodiments, the external system is stored on an external computing entity 102, such as an external computing entity 102, such as an external computing entity 102 associated with a medical provider institution and/or a health insurance provider institution. In some of those embodiments, to integrate the qualified predictive model with the particular external system, the external integration engine 113 communicates with the external computing entity 102 associated with the particular external system.

At step/operation 404, the external integration engine 113 generates new prediction input data and new ground-truth data during the external integration performed in step/operation 404. For example, the external integration engine 113 may periodically obtain, from an EMR external system and/or from a point-of-care predictive system, diagnostic information associated with particular patient predictive entities. As another example, the external integration engine 113 may periodically obtain, from an EMR external system and/or from a point-of-care predictive system, health feature information associated with particular patient predictive entities. As a further example, the external integration engine 113 may periodically obtain, from an EMR external system and/or from a point-of-care predictive system, behavioral feature information associated with particular patient predictive entities. As a further example, the external integration engine 113 may periodically obtain, from an EMR external system and/or from a point-of-care predictive system, phenotype feature information associated with particular patient predictive entities.

In some embodiments, after integrating a qualified predictive model with an external system, the external integration engine 113 utilizes the external integration with the external system to obtain feature data and/or ground-truth data that can in turn be utilized to further train predictive models and generate optimized divisions of predictive entities into various predictive cohorts. By utilizing new feature data and/or new ground-truth data to further train predictive models and generate optimized divisions of predictive entities into various predictive cohorts, various embodiments of the present invention enable dynamic refinement and improvement of the predictive models over time through interactions with real-world sources of information. This dynamic refinement and improvement of predictive models, rendered feasible in part because of the training efficiency and reusability of the cohort-based techniques utilized to generate predictive models, enables generation of effective and reliable predictive models that are responsive to real-world changes in data repositories and can thus perform effective and efficient on-demand and real-time predictive data analysis. Such techniques for effective and efficient on-demand and real-time predictive data analysis are especially useful for data intensive domains as well as domains associated with high-dimensionality and/or high cardinality input spaces, such as various medical prediction domains.

In some embodiments, the predictive data analysis computing entity 106 can utilize the qualified predictive model to perform one or more prediction-based actions based on one or more inferred predictions of the qualified predictive model. For example, the predictive data analysis computing entity 106 can utilize the qualified predictive model to generate one or more medical alerts, e.g., one or more alerts to medical provider user profiles and/or one or more alerts to patient user profiles. As another example, the predictive data analysis computing entity 106 can utilize the qualified predictive model to schedule one or more medical appointments. As a further example, the predictive data analysis computing entity 106 can utilize the qualified predictive model to perform one or more operational load balancing systems, e.g., perform operational load balancing actions for a hospital computer system, perform operational load balancing for a provider utilization model associated with a hospital system, perform operational load balancing for a pharmacy institutions based on patient health projections. As yet another example, the predictive data analysis computing entity 106 can utilize the qualified predictive model to generate one or more targeted medical recommendations and/or targeted action recommendations, such as one or more diet plans, one or more drug recommendations, etc.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
receiving, by one or more processors, a plurality of prediction input objects, wherein a prediction input object of the plurality of prediction input objects is indicative of at least one of a phenotype expression or a behavioral quality associated with a predictive entity of a plurality of predictive entities;
generating, by the one or more processors, a factor score indicating a predicted entity-factor relevance of a predictive factor to the predictive entity based on the prediction input object;
generating, by the one or more processors, a qualified predictive model through a plurality of iterations of an iterative cohort generation routine, wherein an iteration of the plurality of iterations comprises:
 (i) determining, by the one or more processors, a factor range for the predictive factor based on a previous iteration preceding the iteration, wherein the factor range is reduced from a previous factor range for the previous iteration,
 (ii) determining, by the one or more processors, one or more predictive cohorts of the plurality of predictive entities based on each the factor score, wherein a predictive cohort of the one or more predictive cohorts is defined by the factor range,
 (iii) generating, by the one or more processors, a predictive model based on the one or more predictive cohorts,
 (iv) generating, by the one or more processors and using the predictive model, an iteration prediction, (v) generating a predictive score for the predictive model based on the iteration prediction, and
(vi) initiating, by the one or more processors and based on a comparison of a predictive score threshold to the predictive score, a subsequent iteration subsequent to the iteration, wherein the subsequent iteration is associated with a subsequent factor range for the predictive factor that is reduced from the factor range for the iteration;

generating, using the qualified predictive model, a prediction for the predictive entity.

2. The computer-implemented method of claim 1, wherein the prediction input object is indicative of a phenotype feature associated with a patient identifier.

3. The computer-implemented method of claim 1, wherein at least one predictive entity of the plurality of predictive entities is associated with a patient identifier.

4. The computer-implemented method of claim 1, wherein the prediction is a health prediction for a patient identifier.

5. The computer-implemented method of claim 1, wherein the predictive score is based on one or more ground-truth predictions associated with the plurality of predictive entities.

6. The computer-implemented method of claim 1, wherein the qualified predictive model is generated in coordination with an external system.

7. The computer-implemented method of claim 6, wherein the external system is an electronic medical record (EMR) system.

8. The computer-implemented method of claim 6, wherein the external system is a point-of-care system.

9. The computer-implemented method of claim 6, wherein the external system is configured to generate one or more new prediction input objects.

10. The computer-implemented method of claim 6, wherein the external system is configured to generate one or more new ground-truth predictions associated with the plurality of predictive entities.

11. An apparatus comprising one or more processors and at least one memory including program code, the at least one memory and the program code configured to, with the one or more processors, cause the apparatus to at least:

receive a plurality of prediction input objects, wherein a prediction input object of the plurality of prediction input objects is indicative of at least one of a phenotype expression or a behavioral quality associated with a predictive entity of a plurality of predictive entities;

generate a factor score indicating a predicted entity-factor relevance of a predictive factor to the predictive entity based on the prediction input object;

generate a qualified predictive model through a plurality of iterations of an iterative cohort generation routine, wherein an iteration of the plurality of iterations comprises:

(i) determining a factor range for the predictive factor based on a previous iteration preceding the iteration, wherein the factor range is reduced from a previous factor range for the previous iteration, (ii) determining one or more predictive cohorts of the plurality of predictive entities based on the factor score, wherein a predictive cohort of the one or more predictive cohorts is defined by the factor range, (iii) generating a predictive model based on the one or more predictive cohorts, (iv) generating, using the predictive model, an iteration prediction, (v) generating a predictive score for the predictive model based on the iteration prediction, and (vi) initiating, based on a comparison of a predictive score threshold to the predictive score, a subsequent iteration subsequent to the iteration, wherein the subsequent iteration is associated with a subsequent factor range for the predictive factor that is reduced from the factor range for the iteration;

generate, using the qualified predictive model, a prediction for the predictive entity.

12. The apparatus of claim 11, wherein at least one predictive entity of the plurality of predictive entities is associated with a patient identifier.

13. The apparatus of claim 11, wherein the prediction is a health prediction for a patient identifier.

14. The apparatus of claim 11, wherein the predictive score is based on one or more ground-truth predictions associated with the plurality of predictive entities.

15. The apparatus of claim 11, wherein the qualified predictive model is generated in coordination with an external system.

16. A computer program product comprising at least one non-transitory computer-readable storage medium having computer-readable program code portions stored therein, the computer-readable program code portions configured to:

receive a plurality of prediction input objects, wherein a prediction input object of the plurality of prediction input objects is indicative of at least one of a phenotype expression or a behavioral quality associated with a predictive entity of a plurality of predictive entities;

generate a factor score indicating a predicted entity-factor relevance of a predictive factor to the predictive entity based on the prediction input object;

generate a qualified predictive model through a plurality of iterations of an iterative cohort generation routine, wherein an iteration of the plurality of iterations comprises:

(i) determining a factor range for the predictive factor based on a previous iteration preceding the iteration, wherein the factor range is reduced from a previous factor range for the previous iteration, (ii) determining one or more predictive cohorts of the plurality of predictive entities based on the factor score, wherein a predictive cohort of the one or more predictive cohorts is defined by the factor range, (iii) generating a predictive model based on the one or more predictive cohorts, (iv) generating, using the predictive model, an iteration prediction, (v) generating a predictive score for the predictive model based on the iteration prediction, and (vi) initiating, based on a comparison of a predictive score threshold to the predictive score, a subsequent iteration subsequent to the iteration, wherein the subsequent iteration is associated with a subsequent factor range for the predictive factor that is reduced from the factor range for the iteration;

generate, using the qualified predictive model, a prediction for the predictive entity.

17. The computer program product of claim 16, wherein at least one predictive entity of the plurality of predictive entities is associated with a patient identifier.

* * * * *